United States Patent
Calleja et al.

(10) Patent No.: US 9,938,545 B2
(45) Date of Patent: Apr. 10, 2018

(54) MODIFIED ALGAE STRAIN AND METHOD OF TRIACYLGLYCEROL ACCUMULATION USING SAID STRAIN

(71) Applicants: FERMENTALG, Libourne (FR); CENTRE NATIONAL DE LA RECHERCHE SCIENTIFIQUE (C.N.R.S), Paris (FR); COMMISARIAT A L'ENERGIE ATOMIQUE ET AUX ENERGIES ALTERNATIVES, Paris (FR)

(72) Inventors: Pierre Calleja, Marlow (GB); Marina Leterrier, Libourne (FR); Eric Marechal, Grenoble (FR)

(73) Assignees: FERMENTALG, Libourne (FR); CENTRE NATIONAL DE LA RECHERCHE SCIENTIFIQUE(C.N.R.S), Paris (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/906,056

(22) PCT Filed: Jul. 21, 2014

(86) PCT No.: PCT/IB2014/002252
§ 371 (c)(1),
(2) Date: Jan. 19, 2016

(87) PCT Pub. No.: WO2015/008160
PCT Pub. Date: Jan. 22, 2015

(65) Prior Publication Data
US 2016/0160247 A1   Jun. 9, 2016

Related U.S. Application Data

(60) Provisional application No. 61/856,378, filed on Jul. 19, 2013.

(51) Int. Cl.
| | | |
|---|---|---|
| *C12P 7/64* | (2006.01) | |
| *C12N 1/12* | (2006.01) | |
| *C12N 15/82* | (2006.01) | |
| *C12N 15/74* | (2006.01) | |
| *C12P 19/34* | (2006.01) | |
| *C12N 9/14* | (2006.01) | |
| *C12N 9/10* | (2006.01) | |

(52) U.S. Cl.
CPC ............ *C12P 7/6463* (2013.01); *C12N 1/12* (2013.01); *C12N 9/1029* (2013.01); *C12N 9/14* (2013.01); *C12N 15/82* (2013.01); *C12Y 203/01051* (2013.01)

(58) Field of Classification Search
CPC ........ C12N 9/14; C12N 9/1029; C12N 15/82; C12N 1/12; C12P 7/6463; C12Y 203/01051
USPC ......... 435/134, 257.2, 470, 471, 91.1, 91.31
See application file for complete search history.

(56) References Cited

U.S. PATENT DOCUMENTS

| | | | |
|---|---|---|---|
| 8,809,026 B2 * | 8/2014 | Vanhercke | C07K 14/415 435/134 |
| 2014/0256927 A1 * | 9/2014 | Bode | C12N 1/12 536/23.1 |

OTHER PUBLICATIONS

Broun et al., Catalytic plasticity of fatty acid modification enzymes underlying chemical diversity of plant lipids. Science, 1998, vol. 282: 1315-1317.*
Cerutti. et al., RNA-mediated silencing in algae: Biological roles and tools for analysis of gene function. Eukaryotic cell, 2011, vol. 10(9): 1164-1172.*
Darzins et al., Current status and potential for algal biofuels production. National renewable energy laboratory report; Report T39-T2, Aug. 6, 2010: 131 pages.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Provasoli et al., The development of artificial media for marine algae. Archiv fur Mikrobiologie, Bd. 25, S. 392-428, 1957.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*

* cited by examiner

*Primary Examiner* — Ganapathirama Raghu
(74) *Attorney, Agent, or Firm* — Browdy and Neimark, PLLC (57) ABSTRACT

The present invention relates to a genetically engineered algae strain in which the expression of the CGI-58 gene or homologous gene thereof is silenced. The present invention further relates to a method of triacylglycerol accumulation using said genetically engineered diatom and/or diatom strain.

6 Claims, 4 Drawing Sheets

FIGURE 1A

Promoter H4    zeocin    AS CGI-58 terminator

FIGURE 1B (1)

CTAAATTGTAAGCGTTAATATTTTGTTAAAATTCGCGTTAAATTTTTGTTAAATCAGCTCATTTTTTA
ACCAATAGGCCGAAATCGGCAAAATCCCTTATAAATCAAAAGAATAGACCGAGATAGGGTTGAGT
GTTGTTCCAGTTTGGAACAAGAGTCCACTATTAAAGAACGTGGACTCCAACGTCAAAGGGCGAAA
AACCGTCTATCAGGGCGATGGCCCACTACGTGAACCATCACCCTAATCAAGTTTTTTGGGGTCGA
GGTGCCGTAAAGCACTAAATCGGAACCCTAAAGGGAGCCCCCGATTTAGAGCTTGACGGGGAAA
GCCGGCGAACGTGGCGAGAAAGGAAGGGAAGAAAGCGAAAGGAGCGGGCGCTAGGGCGCTGG
CAAGTGTAGCGGTCACGCTGCGCGTAACCACCACACCCGCCGCGCTTAATGCGCCGCTACAGG
GCGCGTCCCATTCGCCATTCAGGCTGCGCAACTGTTGGGAAGGGCGATCGGTGCGGGCCTCTT
CGCTATTACGCCAGCTGGCGAAAGGGGGATGTGCTGCAAGGCGATTAAGTTGGGTAACGCCAG
GGTTTTCCCAGTCACGACGTTGTAAAACGACGGCCAGTGAGCGCGCGTAATACGACTCACTATA
GGGCGAATTGGAGCTCGCAATCTCACGCACCAGGCGCTGGAAGGGCAACTTGCGGATGAGAAG
GTCCGTGGACTTCTGGTAACGACGGATCTCACGCAGAGCGACGGTTCCAGGGCGATAACGGTG
GGGCTTCTTGACTCCTCCGGTAGCCGGAGCGGACTTGCGGGCAGCCTTGGTGGCAAGCTGCTT
GCGCGGCGCTTTGCCTCCGGTGGATTTACGGGCGGTTTGCTTGGTTCGGGCCATTTTGACGGTT
TTTTTTACAAGAGAAGAGTTCTTGAAATTTGTGAGGTTAAAGTGTGTGGCTTCCGCCGTAGTCAAG
GAGCGTGCGGTTGCCGATCGCACCGGTACGTTCTGTAGAAATGAACACAGTGTGTTGAATTGAAA
GTATGGCGCAGGTATGGTGTGTGATAAGTAGCAGCCGCGCCGAGACAAACAAACTTTGGTTTCTA
CGACAATCTCTGTAGACAAGTACTAGAAACCCGTTTGAACGAGCATAAATCTGCACCGGCAGGCC
ACCAGACATCGTTTCAACGTAATATTCTACGTAACCATTTTATCCCAGGAAACCTACGGCCTGTGA
ACCACCGAGACGGAGCACTCACAATTCGCTCTCGGCAACAACCGACAATCGTCTTACTCACAGTC
AATACCGAAAACAAACAACAGCCATGGCCAAGTTGACCAGTGCCGTTCCGGTGCTCACCGCGCG
CGACGTCGCCGGAGCGGTCGAGTTCTGGACCGACCGGCTCGGGTTCTCCCGGGACTTCGTGGA
GGACGACTTCGCCGGTGTGGTCCGGGACGACGTGACCCTGTTCATCAGCGCGGTCCAGGACCA
GGTGGTGCCGGACAACACCCTGGCCTGGGTGTGGGTGCGCGGCCTGGACGAGCTGTACGCCG
AGTGGTCGGAGGTCGTGTCCACGAACTTCCGGGACGCCTCCGGCCGGCCATGACCGAGATCG
GCGAGCAGCCGTGGGGGCGGGAGTTCGCCCTGCGCGACCCGGCCGGCAACTGCGTGCACTTC
GTGGCCGAGGAGCAGGACTGACCGACGCCGACCAACACCGCCGGTCCGACGCGGCCCgACGG
GTCCgAGGCCTTCTAGATGGCCCGACTTACTCACTTGATATACATCAACTCGGGGTGCATCTTGA
TTCATTGACCGTTTAGCTTCTgCTGCTTGCTGGACCTGCAATCCACCATTTGAATCCATCCAATCTT
GAGCACCGTACAAAAAGCCTACCGAAGGAACCTTCAAATGGGGAATCCGATGCAAGGCTGGCTC
CTTTGCAAAAATACCAGGCGTCAAGATACGATTAATGCAGTACTCTCCGGATGCGGGCAAGGTGA
CGGCGCTTCGATAGAGGTATTCCGATACCGCGACACGCTCCTTCTCATCATCAATCGCCGGTAAT
CGACGACGTACGTATTCCTGAATCATCCGCTCGCTACGACTAGTGGGTAACATGCGCAGCACGT
CTCCGGGAGTTTGCCGCCCGAACAggTAGTTGAATGTTCCGTACATCAGACGACCCTGCAAGAAT
TCtgagCTACCTCGACTTTGGCTGGGACACTTTCAGTGAGGACAAGAAGCTTCAGAAGCGTGCTAT
CGAACTCAACCAGGGACGTGCGGCACAAATGGGCATCCTTGCTCTCATGGTGCACGAACAGTTG

```
GGAGTCTCTATCCTTCCTTAAAAATTTAATTTTCATTAGTTGCAGTCACTCCGCTTTGGTTTCACAG
TCAGGAATAACACTAGCTCGTCTTCAggtaccCAGCTTTTGTTCCCTTTAGTGAGGGTTAATTGCGC
GCTTGGCGTAATCATGGTCATAGCTGTTTCCTGTGTGAAATTGTTATCCGCTCACAATTCCACACA
ACATACGAGCCGGAAGCATAAAGTGTAAAGCCTGGGGTGCCTAATGAGTGAGCTAACTCACATTA
ATTGCGTTGCGCTCACTGCCCGCTTTCCAGTCGGGAAACCTGTCGTGCCAGCTGCATTAATGAAT
CGGCCAACGCGCGGGGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTACCGGATACCTGTCC
GCCTTTCTCCCTTCGGGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTGAAGTGGTG
GCCTAACTACGGCTACACTAGAAGGACAGTATTTGGTATCTGCGCTCTGCTGAAGCCAGTTACCT
TCGGAAAAAGAGTTGGTAGCTCTTGATCCGGCAAACAAACCACCGCTGGTAGCGGTGGTTTTTT
GTTTGCAAGCAGCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGATTATCAAAAAG
GATCTTCACCTAGATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCAATAAACCA
GCCAGCCGGAAGGGCCGAGCGCAGAAGTGGTCCTGCAACTTTATCCGCCTCCATCCAGTCTATT
AATTGTTGCCGGGAAGCTAGAGTAAGTAGTTCGCCAGTTAATAGTTTGCGCAACGTTGTTGCCAT
TGCTACAGGCATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTTCGGTCCTCCG
ATCGTTGTCAGAAGTAAGTTGGCCGCAGTGTTATCACTCATGGTTATGGCAGCACTGCATAATTCT
CTTACTGTCATGCCATCCGTAAGATGCTTTTCTGTGACTGGTGAGTACTCAACCAAGTCATTCTGA
GAATAGTGTATGCGGCGACCGAGTTGCTCTTGCCCGGCGTCAATACGGGATAATACCGCGCCAC
ATAGCAGAACTTTAAAAGTGCTCATCATTGGAAAACGTTCTTCGGGGCGAAAACTCTCAAGGATCT
TACCGCTGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGAATAAG
GGCGACACGGAAATGTTGAATACTCATACTCTTCCTTTTTCAATATTATTGAAGCATTTATCAGGGT
TATTGTCTCATGAGCGGATACATATTTGAATGTATTTAGAAAAATAAACAAATAGGGGTTCCGCGC
ACATTTCCCCGAAAAGTGCCAC
```

MODIFIED ALGAE STRAIN AND METHOD OF TRIACYLGLYCEROL ACCUMULATION USING SAID STRAIN

FIELD OF THE INVENTION

The present invention relates to a modified algae strain in which the activity of the protein CGI-58 or one of its homologous has been modified in order to permit the accumulation of oil, advantageously of triacylglycerol.

More precisely in one of its preferred embodiment the expression of the CGI-58 gene or homologous gene thereof is silenced or attenuated. The present invention further relates to a method of triacylglycerol accumulation using said modified strain.

BACKGROUND

Diatoms are a major phylum of the phytoplankton biodiversity in oceans, fresh water and various soil habitats. They are responsible for up to 25% of the global primary productivity. Study of this group of eukaryotes has benefited from recent developments on two species, *Phaeodactylum tricornutum*, a model of pennate diatoms and *Thalassiosira pseudonana*, a model of marine centric diatoms, for which intense efforts have been put to sequence their genomes, define reference data for transcriptome and whole-cell proteome studies, and eventually develop molecular tools to speed up functional analyses. Molecular tools thus allow the deciphering of the role of proteins by gene knockdown technologies (RNAi) and functional characterization of obtained genetically engineered lines. Availability of models for both pennate and centric diatoms is also essential to address common or specific features of these two groups.

Diatoms, like other microalgae, are considered a plausible alternative source of hydrocarbons to replace fossil fuels, with the advantage of having a neutral $CO_2$ balance, based on the hypotheses that $CO_2$ and water can be efficiently converted into biomass by photosynthesis and that the carbon metabolism could be controlled so that they accumulate energetically-rich triacylglycerol (TAG, also called oil). Different phytoplanktonic organisms of the *Chromalevolata superphylum* have focused the attention for their ability to accumulate TAG, with promising initial yields and appropriate robustness and physical properties to be implemented in an industrial process, including *P. tricornutum*. *P. tricornutum* is currently used for the industrial production of omega-3 polyunsaturated fatty acids but industrial implementation for biofuels is still limited by the growth retardation and low yield in biomass when TAG accumulation is triggered using conventional nutrient starvation approaches, such as nitrogen starvation. *P. tricornutum* exhibits interesting properties for an industrial implementation, like the ability to grow in the absence of silicon or the sedimentation of cells that could be useful for harvesting techniques. Progresses in genetic engineering and farming performances are therefore needed for biofuel applications. Attempts to promote TAG accumulation can rely on various strategies that can be combined, including the stimulation of fatty acid and TAG biosynthesis, the blocking of pathways that divert carbon to alternative metabolic routes and eventually the arrest of TAG catabolism.

Many proteins associate with oil droplets and control the storage or release of TAG used for energy, membrane biogenesis or signaling. The CGI-58 (comparative gene identification 58), an α/β hydrolase-type protein primarily, is one of these lipid droplet proteins involved in TAG hydrolysis in mammals. In mice, CGI-58 knockdown thus induced a 4-fold increase in hepatic cells. A CGI-58 homolog exists in angiosperms and its knock out in *Arabidopsis* led to the accumulation of oil droplets in leaf tissues, which normally do not store lipids. In mammals, the activity of CGI-58 is regulated by a protein called perilipin. No homologs of this protein have been identified in angiosperms. In *Arabidopsis*, CGI-58 was shown to interact with PXA1, a fatty acid transporter at the surface of peroxisomes, feeding peroxisomal β-oxidation catabolic route. Thus, CGI-58 appears as a protein localized at the surface of oil droplets and interacting with various protein partners from animals to plants, involved in TAG catabolism. The action of CGI-58 occurs therefore by different mechanisms in different organisms, with distinct protein partners following the species (e.g. perilipin in mammals or PXA1 in angiosperms). Potential protein partners in diatoms have not been demonstrated.

Description

The present invention relates to a modified protist strain in which the activity of the protein CGI-58 or one of its homologous has been modified in order to permit the accumulation of oil, advantageously of triacylglycerol.

In the present text modified means that the algae strain has been manipulated in order to activate or decrease, eventually until the complete inhibition, the CGI-58 protein activity. Preferably according to the invention the activity of the CGI-58 protein is decrease or completely inhibited.

Many technics are known to alter the expression of a protein. It is possible to cite the technics that alter the gene coding the protein or its expression as for example by mutation, insertion, deletion, RNAi inhibition. These types of technics can be grouped under the term "genetically engineered".

It is also possible to cite technics that alter the transcription of the gene or the translation of the RNA issued from the transcription of the gene.

It is also possible to cite technics that use at least a compound like a chemical compound or a biological compound (antibody for example) that will alter the activity of the protein for example by binding to it.

According to the invention all known methods that permit to modify the activity of the CGI-58 protein can be used.

According to the invention one of the preferred methods is to genetically modify the expression of the CGI-58 gene or homologous gene thereof in order to at least attenuate its expression, preferably to silence it.

Preferably, the protist organism or protist strain belongs to the kingdom Chromalveolata.

The present invention thus relates to a modified strain of a species belonging to the kingdom Chromalveolata, in which the CGI-58 protein or one of its homologous has been modified in order to permit the accumulation of oil in the strain, advantageously accumulation of triacylglycerol. According to the invention the activity of said protein is impaired, ie at least reduced, preferentially abolished.

In one embodiment of the invention the expression of the CGI-58 gene or any homologous gene thereof is attenuated or silenced (for example, by knocking down).

If the gene is silenced, there is no gene expression and CGI-58 protein synthesis.

If the gene is attenuated, the expression of the gene and the synthesis of CGI-58 protein are decreased of at least 50%, preferably of at least 70% and more preferably at least 90%.

More preferably, the modified strain is respectively a diatom or diatom strain, still more preferably a pennate diatom or a pennate diatom strain.

Advantageously, the pennate diatom or pennate diatom strain is of the *Phaeodactylum* genus, and more preferably of the strain *Phaeodactylum tricornutum*.

An example of *Phaeodactylum tricornutum* strain is *Phaeodactylum tricornutum* (Pt1) Bohlin Strain 8.6 CCMP2561 (Culture Collection of Marine Phytoplankton, now known as NCMA: National Center for Marine Algae and Microbiota).

"Homologuous sequence" as used herein refers to a sequence involved in triacylglycerol (TAG) catabolism and having similarity or identity with CGI-58 sequence, with identity being preferred. Homology can be determined using standard techniques known in the art.

In particular, by "% identity" with respect to the *homo sapiens* CGI-58 sequence is defined herein as the percentage of amino acid residue in a candidate sequence that are identical with the amino acid residues in the CGI-58 sequence, after aligning the sequences and introducing gaps, if necessary, to achieve the maximum percent sequence identity, and not considering any conservative substitutions as part of the sequence identity. The % identity values used herein are generated by EMBOSS (6.3.1) (The European Molecular Biology Open Software Suite (2000) Rice, P. Longden, I. and Bleasby, A. Trends in Genetics 16, (6) pp 276-277).

By "% similarity" with respect to the *homo sapiens* CGI-58 sequence is defined herein as the percentage of amino acid residues in a candidate sequence that are conserved compared to the amino acid residues in the *homo sapiens* CGI-58 sequence, after aligning the sequences and introducing gaps, if necessary, to achieve the maximum percent sequence similarity. So the "% similarity" is the "% identity" plus the percentage of conserved substitution (ie: aspartate for glutamate). The % similarity values used herein are generated by EMBOSS (6.3.1).

Preferably, the homologous gene of the CGI-58 presents at least 15% similarity, at least 20% similarity, more preferably at least 25% similarity and still more preferably at least 30% similarity with the *Homo sapiens* CGI-58 sequence.

Preferably, the homologous gene of the CGI-58 presents at least 15% identity, and more preferably, at least 20% identity with the *Homo sapiens* CGI-58 sequence.

As an example, the following data, relating to the *Homo sapiens* CGI-58 gene and different homologuous genes thereof, can be given:

Homo sapiens (CAD12731)/*Arabidopsis thaliana* (ABM06019): identity 26.8%, similarities 41.5°%

Homo sapiens (CAD12731)/*Phaeodactylum tricornutum* (XP_002183583): identity 21.6%, similarities 32.2%

Homo sapiens (CAD12731)/*Thalassiosira pseudonana* (XP_002294083) non complete sequence: identity 19.3%, similarities 32.1%

*Arabidopsis thaliana* (ABM06019)/*Phaeodactylum tricornutum* (XP_002183583): identity 26%, similarities 42.6%

*Arabidopsis thaliana* (ABM06019)/*Thalassiosira pseudonana* (XP_002294083) non Complete sequence: identity 20%, similarities 29.1%

*Phaeodactylum tricornutum* (XP_002183583)/*Thalassiosira pseudonana* (XP_002294083) non complete sequence: identity 30.9%, similarities 41.2%

Alternatively, the CGI-58 sequence of reference for the evaluation of the similarity can be the *Phaeodactylum tricornutum* sequence mentioned above.

The modified strain according to the invention can accumulate or contain at least 1.5 fold, preferably 4 fold, the triacylglycerol content of the corresponding wild type strain.

By "corresponding wild type strain", it is meant the strain, before the modification aiming at silencing or attenuating the CGI-58 protein activity, preferably the expression of the CGI-58 gene or any homologous gene thereof (i.e. untransformed organism or strain).

Indeed, the inventors have shown that protists harboring the silencing construction contain more oil (>than 1.5 fold increase). In particular, the invention allows to reach a 4 fold increase. Additionally, they have also shown that:

Protists harboring the silencing construction contain more oil in growing medium (such as ESAVV) containing nitrogen (also called "nitrogen enriched medium", such as Sodium Nitrate, $NaNO_3$ 0.05 g/L or 0.034 g/L of N element) or depleted of nitrogen (no addition) than wild type untransformed cells;

Protists harboring the silencing construction contain more oil than wild type untransformed cells;

Protists harboring the silencing construction accumulate oil earlier than wild type untransformed cells;

The accumulation of oil occurs in the early logarithm phase of growth;

The accumulation of oil does not correlate with a retardation of growth.

The present invention further discloses a method of preparation of a genetically engineered organism or strain according to the invention, comprising the transformation of an organism with a vector expressing RNAi construction designed to target the expression of the CGI-58 gene or any homologous gene thereof.

Advantageously, the vector is introduced in the organism by biolistic methods (particle bombardment) or electroporation.

After transformation, organisms in which the expression of the CGI-58 gene or any homologous gene thereof is attenuated or silenced, are selected and cultured.

The present invention further discloses a method of accumulation of triacylglycerol in an organism belonging to the kingdom Chromalveolata, comprising the step of silencing the expression of the CGI-58 gene or any homologous gene thereof in said organism.

Advantageously, in said method of accumulation, the organism is cultured in an nitrogen-containing medium or alternatively in a nitrogen-depleted medium.

After 1 day (preferably 3 days) in the culture medium, the genetically engineering organisms are harvested and triacylglycerols are recovered.

The invention further encompasses the use of a genetically engineered organism or strain according to the invention for the production of triacylglycerol(s).

More details and specificities of the invention would appear in the following examples and figures.

FIG. 1 describes the *Phaeodactylum tricornutum* CGI-58 silencing strategy used in the invention.

pH4: H4 promoter;
AS: antisense fragment corresponding to CGI-58;
Ter: Terminator sequence.

WT: *P. tricornutum* wild type.
(+N): nitrogen-rich culture medium
(−N): nitrogen starved culture medium.

FIG. 4A. Growth curve and oil accumulation over time. Oil was determined during growth. Results obtained for *P. tricornutum* containing CGI-58 antisense are (-■-) compared to those obtained with the *P. tricornutum* wild type (WT) (-♦-).

FIG. 4B. Microscopy observation of oil accumulation using Nile Red probe.

EXAMPLE 1: TRANSFORMATION OF *P. TRICORNUTUM* BY SILENCING THE CGI-58 GENE EXPRESSION AND ACCUMULATION OF OIL

1. Material and Methods

*Phaeodactylum tricornutum* Strain and Growth Conditions.

*Phaeodactylum tricornutum* (Pt1) Bohlin Strain 8.6 CCMP2561 (Culture Collection of Marine Phytoplankton, now known as NCMA: National Center for Marine Algae and Microbiota) was used in all experiments (Berges J A et al., 2001, J Phycol 37:1138-1145), Pt1 was grown at 20° C. in 250 mL flask using enriched artificial seawater (ESAW) medium. Cells were grown on a 12:12 light (450 $\mu E^{-1}$ sec$^{-1}$)/dark cycle. Cells were sub-cultured every week by inoculate fresh media with 1/5 of previous culture. Nitrogen-starved N(−) medium contained no source of nitrogen. Nitrogen-replete N(+), medium contained 0.05 g/L NaNO$_3$.

Genetic Construction for CGI-58 Silencing.

Genomic DNA was extracted from *Phaeodactylum tricornutum* Pt1 strain using the following procedure: 100 mg fresh Pt cells were flash frozen in liquid nitrogen and homogenized in 400 µl of extraction buffer (Tris-HCl 200 mM, pH 7.5; NaCl 250 mM; EDTA 25 mM; SDS 0.5%, w/v). After a 5 minutes centrifugation at 10,000×g, the supernatant was transferred to the same volume of isopropanol to precipitate DNA. After an additional 15 minutes centrifugation at 10,000×g, the pellet was washed with ethanol 70%, dried and solubilized in water. DNA concentration was measured using a Nanodrop 2000 spectrophotometer (Thermo Scientific), and quality was checked by electrophoresis on agarose gel. Using genomic DNA as matrix, a 436-pb sequence was amplified by polymerase chain reaction (PCR) with the following primers designed from XM_002183547 (Pt CGI.58 homolog), and carrying respectively EcoRI and XbaI restriction sites (underlined sequence): Pt.CGI-58.AS.F TC GAATTCTTGCAGGGTCGTCTGATGTA (SEQ ID NO:1), Pt.CGI-58.AS.R CTAGA TCTAGATGGCCCGACTTACTCACT (SEQ ID NO:2). PCR was performed with a S1000™ Thermal Cycler (Biorad laboratory inc.) using Phusion High Fidelity polymerase (Thermo Scientific) according to the manufacturer's instructions. PCR product was digested by EcoR I and Xba I, purified and cloned in the linearized expression vector.

The expression vector used for silencing was generated from the anti-sense vector hla (name in the princeps publication of De Riso and collaborator: "h" stands for promoter H4, "l" for "long fragment of this promoter" and "a" for antisense developed previously (De Riso V et al, 2009, Nucleic Acids Res 37:e96), and harbouring a β-Glucuronidase (GUS) reporter sequence.

The GUS 250 pb fragment was excised from hla with EcoR I and Xba I. Ligation mixture of linear excised hla vector and 436 pb CGI-38 anti-sense fragment was then transformed into DH5α *Escherichia coli*. Positive colonies were identified by PCR, and products were subsequently sequenced.

First Method for Transformation: Biolistic Transformation

Vectors were introduced into *P. tricornutum* by microparticle bombardment using a Biolistic PDS-1000/He Particle Delivery System (Bio-Rad, Hercules, Calif., USA), as previously described (Falciatore A et al., 1999, Mar Biotechnol (NY) 1:239-251), fitted with 1,550 psi rupture discs. Tungsten particles (M-17) were coated with 1 µg of plasmid DNA, previously linearized by Pvu II, in the presence of CaCl$_2$ and spermidine. One hour prior to bombardment, approximately 5.10$^7$ cells were spread in the center of a plate containing 20 ml of solid culture medium (ESAW medium, agar 1%). The plates were positioned at the second level within the biolistic chamber for bombardment. Bombarded cells were then allowed to recover for 48 h before being suspended in 1 mL of ESAW medium. 500 µl of this suspension were plated onto a solid medium containing 75 µg/mL zeocin. After two to four weeks of incubation in white light (175 µmol m$^{-2}$·s$^{-1}$; 12 h photoperiod) at 20° C., individual resistant colonies were collected and streaked on fresh ESAW agar plates supplemented with zeocin 75 µg·mL$^{-1}$ and inoculated into liquid ESAW medium for further analyses. Presence of the transgene in *Phaeodactylum tricornutum* was eventually validated by PCR amplification using genomic DNA of resistant colonies.

Second Method of Transformation: Electroporation

Vectors were introduced into *P. tricornutum* by electroporation with multiple pulses, following the method described by Miyahara et al (2013) Biosci. Biotechnol. Biochem, 77:120936-1-3. Other electroporation methods with multiple pulses can be used.

Nile Red Staining of Oil Droplets

Accumulation of oil droplets was monitored by Nile Red (Sigma Aldrich) fluorescent staining (Excitation wavelength at 485 nm; emission at 525 nm) as previously described (Cooksey K E et al, 1987, J. Microbiol. Meth. 6:333-345). In brief, cells were diluted and adjusted to a cell density that was linearly correlated with Nile Red fluorescence. Nile Red solution (40 µl of 2.5 µg/mL stock concentration, in 100% DMSO) was added to 160 µl cell suspension. Specific fluorescence was determined by dividing Nile Red fluorescence intensity by the number of cells. Oil bodies stained with Nile Red were then visualized using a Zeiss AxioScope.A1 microscope (FITC filter; Excitation wavelength at 488 nm; emission at 519 nm).

Triacylglycerol (TAG) Extraction, Separation by Thin Layer Chromatography, Quantification and Analysis.

Triacylglycerol were extracted from 200 mg of freeze-dried *Phaeodactylum tricornutum* cells, according to Domergue F et al., 2003, Plant Physiol 131:1648-1660, in order to prevent lipid degradation. Briefly, cells were frozen in liquid nitrogen immediately after harvest. The freeze-dried cell pellet was resuspended in 4 mL of boiling ethanol for 5 minutes followed by the addition of 2 mL of methanol and 8 mL of chloroform at room temperature. The mixture was then saturated with argon and stirred for 1 h at room temperature. After filtration through glass wool, cell remains were rinsed with 3 mL of chloroform/methanol 2:1, v/v. In order to initiate biphase formation, 5 mL of NaCl 1% was then added to the filtrate. The chloroform phase was dried under argon before re-solubilization of the lipid extract in pure chloroform. To isolate TAG, lipids were run on silica gel thin layer chromatography (TLC) plates (Merck) with hexane:diethylether:acetic acid (70:30:1, v/v). Lipids were then visualized under UV light after pulverization of 8-anilino-1-naphthalenesulfonic acid at 2% in methanol. They were then scraped off from the TLC plates for further analyses. For acyl profiling and quantification of TAG, fatty acids were methylated using 3 mL of 2.5% $H_2SO_4$ in methanol during 1 h at 100° C. (including standard amounts of 21:0). The reaction was stopped by the addition of 3 mL of water and 3 mL of hexane. The hexane phase was analyzed by gas liquid chromatography (Perkin Elmer) on a BPX70 (SGE) column. Methylated fatty acids were identified by comparison of their retention times with those of standards and quantified by surface peak method using 21:0 for calibration. Extraction and quantification were done at least 3 times.

2. Results

Generation of *Phaeodactylum Tricornutum* Expressing a CGI-38 Anti-Sense Construction.

Figure 1A:
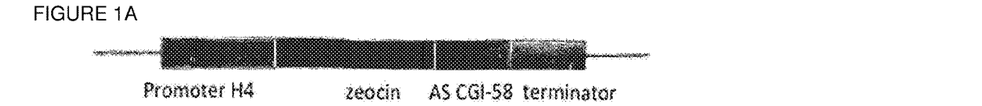
FIG. 1A shows a schematic representation of the hla-CGI-58 construct used for the transformation.
Figure 1B:
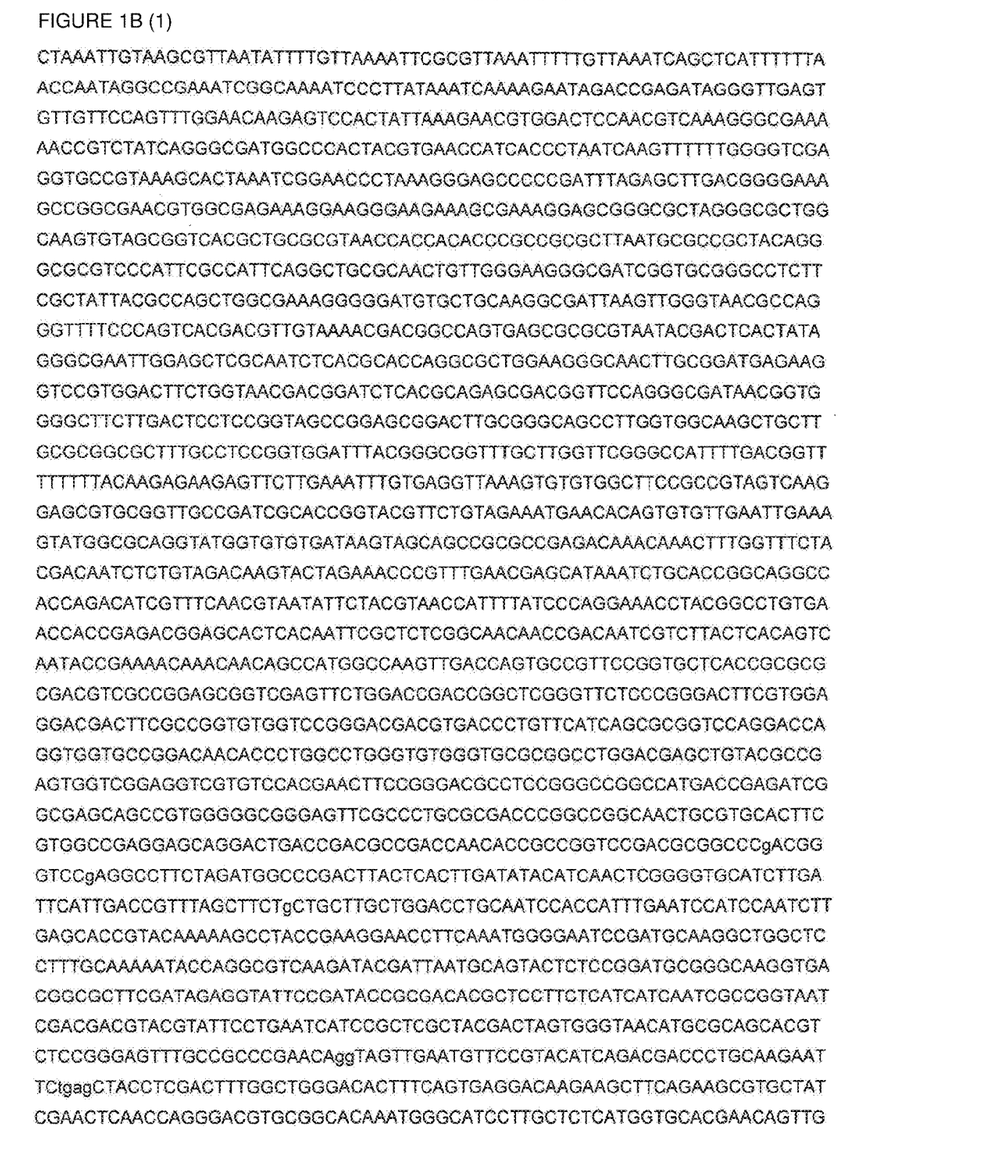
FIG. 1B shows the complete sequence (SEQ ID NO:3) of the vector harboring the CGI-58 antisense sequence.
Figure 2:
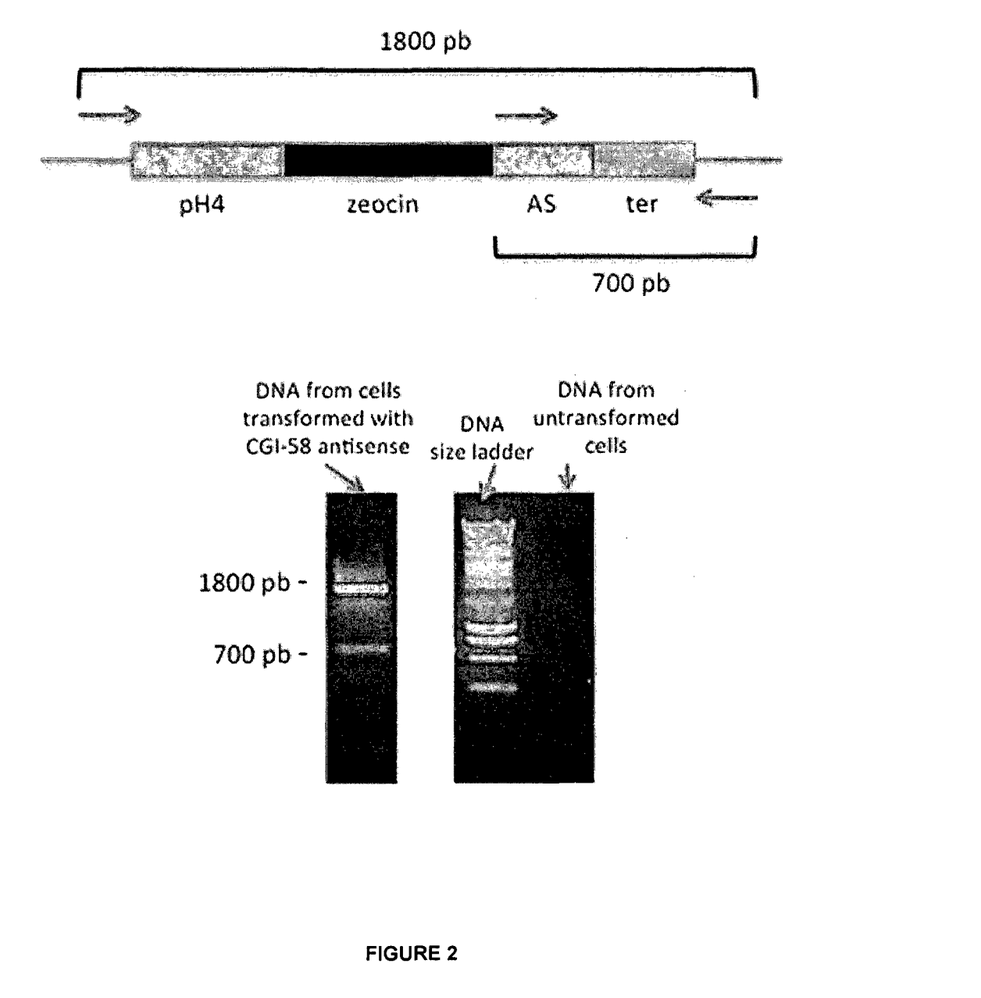
FIG. 2 describes a schematic representation of the polymerase chain reaction validation of genetic transformation of *Phaeodactylum*. Arrows represent the PCR primers used in the experiment. Amplified fragments (1800 pb and 700 pb) are only observed in transformed cells, not in untransformed cells.

Only one single gene coding for a CGI-58 homolog (genbank XM_002183547; Phatrdraft 54974) was predicted in the *P. tricornutum* genome by conventional BlastP similarity search (Altschul S F et al., 1990, Journal of Molecular Biology 215:403-410). To drive Phatrdraft 54974 silencing, a vector whose expression was under control of the H4 promoter was constructed (De Riso V et al, 2009, Nucleic Acids Res 37:e96). The expression vector used for silencing was generated from the anti-sense vector hla (name in the princeps publication of De Riso and collaborator: "h" stands for promoter H4, "l" for "long fragment of this promoter" and "a" for antisense developed previously (De Riso V et al, 2009, Nucleic Acids Res 37:e96). This hla vector has been modified so as to remove the antisense fragment it initially contained corresponding to a GUS fragment, and introduce an antisense fragment corresponding to CGI-58. The targeted region for silencing corresponded to the end portion of the Phatrdraft 54974/CGI-58 sequence (FIG. 1).

Following *Phaeodactylum* transformation using a particle gun or electroporation, transformed cells were selected under zeocine selection pressure and putative silenced clones were selected. The knockdown of the endogenous CGI-58 gene was then controlled by quantitative RT-PCR using primers corresponding to a full length transcription.

Figure 3:
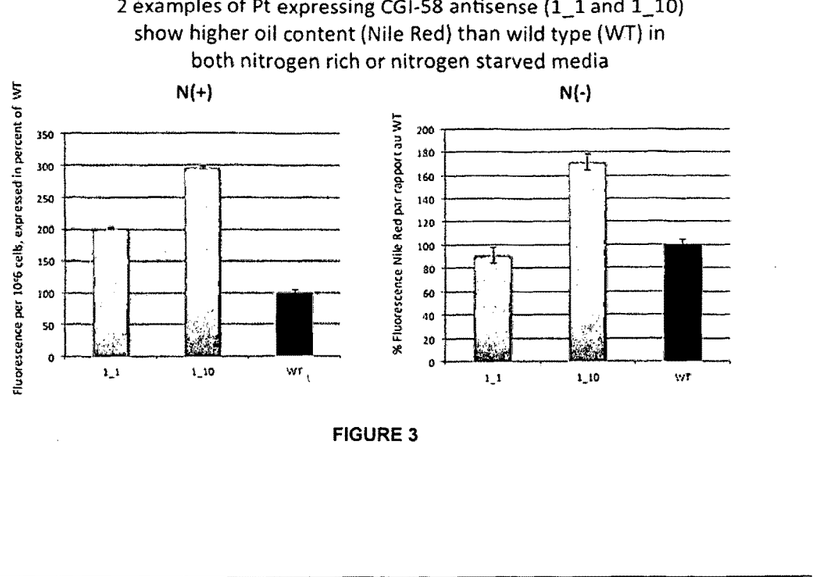
FIG. 3 describes the screening of *Phaeodactylum tricornutum* transformed with the CGI-58 antisense construct based Nile Red specific fluorescence intensity.1_1, 1_10: CGI-58 antisense expressing lines obtained according the invention after transformation of *P. tricornutum* wild type strain with the CGI-58 antisense expression vector obtained according to "Genetic construction for CGI-58 silencing".

In the absence of specific antibodies, the actual level of CGI-58 level could not be assessed. Nevertheless, a simple cell-based assay allows the functional analysis of CGI-58 in the catabolism of oil bodies. Transformed cells were thus screened using a Nile Red assay, directly monitoring the accumulation of oil within cells in nitrogen-rich (+N) or starved (−N) media (FIG. 3). An increased amount of Nile Red staining is observed compared to wild-type levels (FIG. 3). Very interestingly, the higher level of oil that accumulates in CGI-58 antisense expressing lines, such as in line 1_10, was observed in both nitrogen-rich and nitrogen-starved conditions.

Following *P. tricornutum* transformation with CGI-58 antisense construct, cells were grown for 5 days, and then freshly sub-cultured in a medium containing nitrogen or missing this nutrient. Cells were analyzed after 2 days growth in ESAW medium, with or without nitrogen. Nile Red (NR) fluorescence was measured using a fluorimeter, and was expressed per $10^6$ cells. The initial vector expressing a GUS anti-sense (hla) was used as a vector control and showed no difference with WT. WT, untransformed wild type cells.

Figure 4:
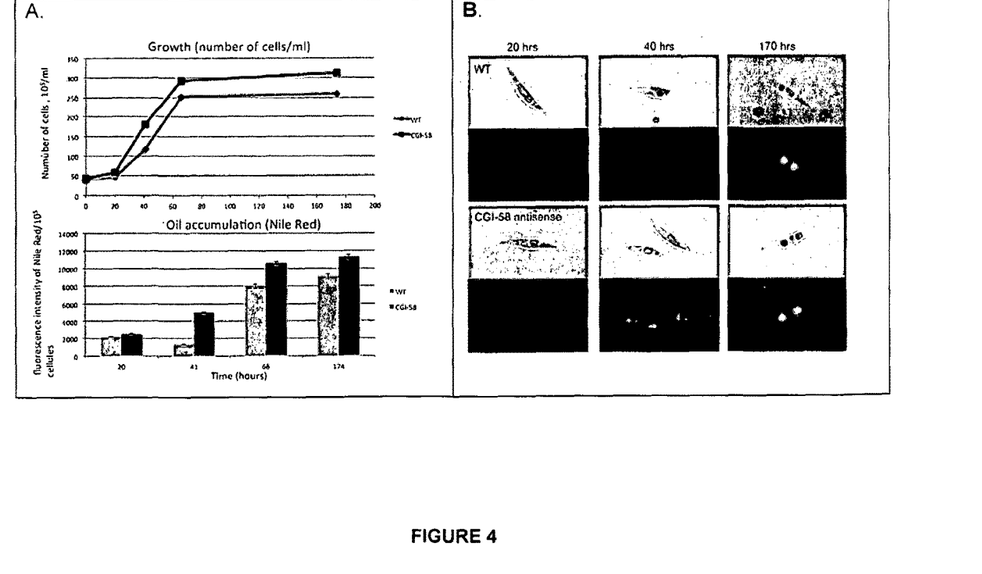
FIG. 4: Growth and accumulation of oil bodies in *Phaeodactylum tricornutum* transformed with the CGI-58 antisense construct.

We compared the growth of untransformed and transformed cells, monitored in parallel in ESAW medium. As shown in FIG. 4A, growth shows no retardation and is comparable between transformed and untransformed cells.

We then analyzed the phenotype of cells and oil droplets in both untransformed and transformed cells. As shown in FIG. 4B, oil droplets appear early during the growth, with the formation of multiple droplets that seem to converge to form two large droplets on each side of the nucleus.

The invention claimed is:

1. A genetically engineered strain of *Phaeodactylum tricornutum*, in which the activity of the comparative gene identification 58 (CGI-58) protein has been modified in order to permit the accumulation of oil in the strain, advantageously accumulation of triacylglycerol, wherein the activity of the CGI-58 is modified by silencing or attenuating the expression of the CGI-58 gene.

2. A genetically engineered strain according to claim 1, which accumulates or contains at least 1.5-fold the triacylglycerol content of the corresponding wild type strain.

3. A genetically engineered strain according to claim 2, which accumulates or contains at least 4 fold the triacylglycerol content of the corresponding wild type strain.

4. A method of preparation of a genetically engineered strain of *Phaeodactylum tricornutum* as described in claim 1, comprising transforming said strain with a vector expressing RNAi construction designed to target the expression of the CGI-58 gene.

5. The method according to claim 4, wherein the vector is introduced in the strain by particle bombardment or electroporation.

6. A method for increasing accumulation of triacylglycerol in a strain of *Phaeodactylum tricornutum*, comprising the step of altering or silencing the expression of the CGI-58 gene in said organism.

* * * * *

SEQUENCE LISTING

```
<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: PCR primer

<400> SEQUENCE: 1
tcgaattctt gcagggtcgt ctgatgta                                        28

<210> SEQ ID NO 2
<211> LENGTH: 29
<212> TYPE: DNA
<213> ORGANISM: Artificial Sequence
<220> FEATURE:
<223> OTHER INFORMATION: PCR primer

<400> SEQUENCE: 2
ctagatctag atggcccgac ttactcact                                       29
```

<210> SEQ ID NO 3
<211> LENGTH: 4611
<212> TYPE: DNA
<213> ORGANISM: Artificial Sequence
<220> FEATURE:
<223> OTHER INFORMATION: Complete sequence of the vector harboring the
      CGI-58 antisense sequence

<400> SEQUENCE: 3

```
ctaaattgta agcgttaata ttttgttaaa attcgcgtta aattttttgtt aaatcagctc      60
attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta atcggaacc ctaaagggag      300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggt ttttcccagt cacgacgttg     600
taaaacgacg gccagtgagc gcgcgtaata cgactcacta gggcgaat tggagctcgc       660
aatctcacgc accaggcgct ggaagggcaa cttgcgatg agaaggtccg tggacttctg      720
gtaacgacgg atctcacgca gagcgacggt tccagggcga taacggtggg gcttcttgac    780
tcctccggta gccggagcgg acttgcgggc agccttggtg gcaagctgct tgcgcggcgc    840
tttgcctccg gtggatttac gggcggtttg cttggttcgg gccatttttga cggttttttt    900
tacaagagaa gagttcttga aatttgtgag gttaaagtgt gtggcttccg ccgtagtcaa    960
ggagcgtgcg gttgccgatc gcaccggtac gttctgtaga aatgaacaca gtgtgttgaa   1020
ttgaaagtat ggcgcaggta tggtgtgtga taagtagcag ccgcgccgag acaaacaaac   1080
tttggtttct acgacaatct ctgtagacaa gtactagaaa cccgtttgaa cgagcataaa   1140
tctgcaccgg caggccacca gacatcgttt caacgtaata ttctacgtaa ccattttatc   1200
ccaggaaacc tacggcctgt gaaccaccga dacggagcac tcacaattcg ctctcggcaa    1260
caaccgacaa tcgtcttact cacagtcaat accgaaaaca aacaacagcc atggccaagt   1320
tgaccagtgc cgttccggtg ctcaccgcgc gcgacgtcgc cggagcggtc gagttctgga   1380
ccgaccggct cgggttctcc cgggacttcg tggaggacga cttcgccggt gtggtccggg   1440
acgacgtgac cctgttcatc agcgcggtcc aggaccaggt ggtgccggac aacaccctgg   1500
cctgggtgtg ggtgcgcggc ctggacgagc tgtacgccga gtggtcggag gtcgtgtcca   1560
cgaacttccg ggacgcctcc gggccggcca tgaccgagat cggcgagcag ccgtgggggc   1620
gggagttcgc cctgcgcgac ccggccggca actgcgtgca cttcgtggcc gaggagcagg   1680
actgaccgac gccgaccaac accgccggtc cgacgcggcc cgacgggtcc gaggccttct   1740
agatggcccg acttactcac ttgatataca tcaactcggg gtgcatcttg attcattgac   1800
cgtttagctt ctgctgcttg ctggacctgc aatccaccat ttgaatccat ccaatcttga   1860
gcaccgtaca aaaagcctac cgaaggaacc ttcaaatggg gaatccgatg caaggctggc   1920
tcctttgcaa aaataccagg cgtcaagata cgattaatgc agtactctcc ggatgcgggc   1980
aaggtgacgc gcttcgata gaggtattcc gataccgcga cacgctccctt ctcatcatca   2040
atcgccggta atcgacgacg tacgtattcc tgaatcatcc gctcgctacg actagtgggt   2100
```

```
aacatgcgca gcacgtctcc gggagtttgc cgcccgaaca ggtagttgaa tgttccgtac      2160
atcagacgac cctgcaagaa ttctgagcta cctcgacttt ggctgggaca cttcagtga       2220 ggacaagaag cttcagaagc gtgctatcga actcaaccag ggacgtgcgg cacaaatggg      2280
catccttgct ctcatggtgc acgaacagtt gggagtctct atccttcctt aaaaatttaa      2340
ttttcattag ttgcagtcac tccgctttgg tttcacagtc aggaataaca ctagctcgtc      2400
ttcaggtacc cagcttttgt tccctttagt gagggttaat tgcgcgcttg gcgtaatcat      2460
ggtcatagct gtttcctgtg tgaaattgtt atccgctcac aattccacac aacatacgag      2520
ccggaagcat aaagtgtaaa gcctggggtg cctaatgagt gagctaactc acattaattg      2580
cgttgcgctc actgcccgct ttccagtcgg gaaacctgtc gtgccagctg cattaatgaa      2640
tcggccaacg cgcggggaga ggcggtttgc gtattgggcg ctcttccgct tcctcgctca      2700
ctgactcgct gcgctcggtc gttcggctgc ggcgagcggt atcagctcac tcaaaggcgg      2760
taatacggtt atccacagaa tcaggggata acgcaggaaa gaacatgtga gcaaaaggcc      2820
agcaaaaggc caggaaccgt aaaaaggccg cgttgctggc gttttccat aggctccgcc       2880 cccctgacga gcatcacaaa aatcgacgct caagtcagag gtggcgaaac ccgacaggac      2940
tataaagata ccaggcgttt ccccctggaa gctccctcgt gcgctctcct gttccgaccc      3000
tgccgcttac cggatacctg tccgccttt tcccttcggg aagcgtggcg ctttctcata       3060
gctcacgctg taggtatctc agttcggtgt aggtcgttcg ctccaagctg ggctgtgtgc      3120
acgaaccccc cgttcagccc gaccgctgcg ccttatccgg taactatcgt cttgagtcca      3180
acccggtaag acacgactta tcgccactgg cagcagccac tggtaacagg attagcagag      3240
cgaggtatgt aggcggtgct acagagttct tgaagtggtg gcctaactac ggctacacta      3300
gaaggacagt atttggtatc tgcgctctgc tgaagccagt taccttcgga aaaagagttg      3360
gtagctcttg atccggcaaa caaaccaccg ctggtagcgg tggtttttt gtttgcaagc       3420 agcagattac gcgcagaaaa aaaggatctc aagaagatcc tttgatcttt tctacggggt      3480
ctgacgctca gtggaacgaa aactcacgtt aagggatttt ggtcatgaga ttatcaaaaa      3540
ggatcttcac ctagatcctt ttaaattaaa aatgaagttt taaatcaatc taagtatat      3600 atgagtaaac ttggtctgac agttaccaat gcttaatcag tgaggcacct atctcagcga      3660
tctgtctatt tcgttcatcc atagttgcct gactccccgt cgtgtagata actacgatac      3720
gggagggctt accatctggc cccagtgctg caatgatacc gcgagaccca cgctcaccgg      3780
ctccagattt atcagcaata aaccagccag ccggaagggc cgagcgcaga agtggtcctg      3840
caactttatc cgcctccatc cagtctatta attgttgccg ggaagctaga gtaagtagtt      3900
cgccagttaa tagtttgcgc aacgttgttg ccattgctac aggcatcgtg gtgtcacgct      3960
cgtcgtttgg tatggcttca ttcagctccg gttcccaacg atcaaggcga gttacatgat      4020
cccccatgtt gtgcaaaaaa gcggttagct ccttcggtcc tccgatcgtt gtcagaagta      4080
agttggccgc agtgttatca ctcatggtta tggcagcact gcataattct cttactgtca      4140
tgccatccgt aagatgcttt tctgtgactg gtgagtactc aaccaagtca ttctgagaat      4200
agtgtatgcg gcgaccgagt tgctcttgcc cggcgtcaat acgggataat accgcgccac      4260
atagcagaac tttaaaagtg ctcatcattg gaaaacgttc ttcggggcga aaactctcaa      4320
ggatcttacc gctgttgaga tccagttcga tgtaacccac tcgtgcaccc aactgatctt      4380
cagcatcttt tactttcacc agcgtttctg ggtgagcaaa aacaggaagg caaaatgccg      4440
caaaaaaggg aataagggcg acacggaaat gttgaatact catactcttc ctttttcaat      4500
```

```
attattgaag catttatcag ggttattgtc tcatgagcgg atacatattt gaatgtattt    4560
agaaaaataa acaaataggg gttccgcgca catttccccg aaaagtgcca c              4611
```